United States Patent [19]

Takahata et al.

[11] 4,349,419

[45] Sep. 14, 1982

[54] PROCESS FOR SEPARATION OF ALKYL PHENOLS BY AZEOTROPIC DISTILLATION

[75] Inventors: Kazunori Takahata, Ohtake; Katsuo Taniguchi, Iwakuni; Tadaaki Fujimoto, Yamaguchi, all of Japan

[73] Assignee: Mitsui Petrochemical Industries Ltd., Tokyo, Japan

[21] Appl. No.: 231,022

[22] Filed: Feb. 3, 1981

Related U.S. Application Data

[63] Continuation of Ser. No. 105,245, Dec. 19, 1979, abandoned.

[30] Foreign Application Priority Data

Dec. 25, 1978 [JP] Japan .................................. 53-158690

[51] Int. Cl.³ .............................................. B01D 3/40
[52] U.S. Cl. ....................................... 203/70; 568/750

[58] Field of Search ........................... 203/52, 58, 70; 568/749–752

[56] References Cited

U.S. PATENT DOCUMENTS

3,337,424  8/1967  Neuworth et al. .................. 203/70

Primary Examiner—Frank Sever
Attorney, Agent, or Firm—Sherman & Shalloway

[57] ABSTRACT

In a process for separating at least two alkyl phenols having close boiling points by azeotropic distillation of a mixture composed of the alkyl phenols with a hydrocarbon azeotroping agent, the improvement wherein said hydrocarbon azeotroping agent is selected from saturated aliphatic hydrocarbons of 9 to 13 carbon atoms having a boiling point of 150° to 190° C. at 760 mmHg.

2 Claims, No Drawings

PROCESS FOR SEPARATION OF ALKYL PHENOLS BY AZEOTROPIC DISTILLATION

This is a continuation, of Application Ser. No. 105,245, filed Dec. 19, 1979, now abandoned.

This invention relates to an improvement in a process for the separation of at least two alkyl phenols having close boiling points by azeotropic distillation of a mixture of the alkyl phenols with a hydrocarbon azeotroping agent. Specifically, this invention relates to an improved process for separating a mixture of alkyl phenols having close boiling points into a higher-boiling alkyl phenol and a lower-boiling alkyl phenol with commercial advantage and an improved separating efficiency without any likelihood of causing coloration attributed to the degeneration of the azeotroping agent and of reducing the quality of the separated alkyl phenols.

More specifically, this invention provides in a process for separating at least two alkyl phenols having close boiling points by azeotropic distillation of a mixture compound of the alkyl phenols with a hydrocarbon azeotroping agent, the improvement wherein said hydrocarbon azeotroping agent is selected from saturated aliphatic hydrocarbons of 9 to 13 carbon atoms having a boiling point of 150° to 190° C. at 760 mmHg.

Various methods such as distillation, crystallization, extraction, adsorption or combinations of these have been suggested heretofore for the separation of a mixture of cresol isomers, a mixture of cresols and xylenols, and mixtures of alkyl phenols including these. Of the exemplified methods, crystallization, extraction and adsorption are not good commercial methods because the separating procedure is complicated, and the efficiency of separating cresols is low. In separating a higher-boiling alkyl phenol and a lower-boiling alkyl phenol from a mixture of at least two alkyl phenols having close boiling points such as a mixture of o-cresol, m-cresol and p-cresol, or a mixture of methylated products of cresol or phenol including phenol, o-cresol, p-cresol, 2,4-xylenol and 2,6-xylenol, a rectifying column having a number of theoretical trays is required, and the distillation should be carried out at a high reflux ratio. In addition to these disadvantages, such a separating procedure also has disadvantages in regard to the amount of heat required and the rate of distillation.

In an attempt to overcome these disadvantages, U.S. Pat. No. 3,397,124 discloses a process for the separation of at least two alkyl phenols having close boiling points by azeotropic distillation with an alkene as an azeotroping agent, especially a branched higher alkene having 10 to 14 carbon atoms and a boiling point within 30° C. of more polar alkyl phenol in said alkyl phenols. This process is limited to the use of alkenes which are unsaturated hydrocarbons, and the use of the trimerization product of methylpropene (iso-butylene) having a boiling point of about 175° to 177° C. is recommended.

The present inventors discovered that the azeotroping agent used in the above U.S. Patent, presumably because of its unsaturated bond, is degenerated and colored relatively easily during the azeotropic distillation procedure and builds up in the distillation bottom which contains alkyl phenols having higher-boiling points, thus making it difficult to obtain these higher-boiling alkyl phenols with high quality, and that this trouble becomes more remarkable when an attempt is made to perform the distillation of the lower-boiling alkyl phenols fully from the top of the distillation tower.

It was also found that there is still room for improvement in the content of lower boiling alkyl phenols in the azeotrope from the top, and the separating efficiency of these alkyl phenols is unsatisfactory.

The present inventors made investigations in order to provide an improved process which can remedy or overcome the defects or disadvantages of the prior art which involves azeotropic distillation using alkenes. These investigations have led to the discovery that the use of an azeotroping agent selected from saturated aliphatic hydrocarbons of 9 to 13 carbon atoms having a boiling point of 150° to 190° C. at 760 mmHg makes it possible to separate a higher-boiling alkyl phenol from a lower-boiling alkyl phenol with an improved separating efficiency without the problem of coloration.

It is an object of this invention therefore to provide an improved process for the separation of at least two alkyl phenols having close boiling points by azeotropic distillation.

The above and other objects of this invention along with its advantages will become more apparent from the following description.

The mixture of at least two alkyl phenols having close boiling points from each other to which the process of this invention is applicable include, for example, a mixture containing at least two cresols such as o-cresol (b.p. about 191° C.) and m-cresol (b.p. about 202° C.), and a mixture of at least one of such cresols and at least one other alkyl phenol having a close boiling point to the cresol. Specific examples of the mixture of at least two alkyl phenols having close boiling points are a mixture of cresol isomers including o-cresol, m-cresol and p-cresol; a mixture of o-cresol and 2,6-xylenol (b.p. about 201° C.); a mixture of o-cresol, p-cresol and 2,6-xylenol; a mixture of o-cresol, p-cresol, 2,4-xylenol (b.p. about 210° C.) and 2,6-xylenol; a mixture of o-cresol, p-cresol, 2,4-xylenol, 2,6-xylenol and 2,4,6-trimethylphenol (b.p. about 221° C.); and a mixture of o-cresol, m-cresol, p-cresol, 2,6-xylenol and 2,4,6-trimethylphenol.

Preferably, the process of this invention is applied to a mixture of at least one cresol and at least one xylenol. Such a preferred mixture is, for example, a methylated product of phenol or cresol, such as the reaction product of phenol or cresol with methanol.

The above-exemplified mixtures of at least two alkyl phenols having close boiling ponts may contain other higher-boiling alkyl phenols, phenols, etc.

According to the process of this invention, the above-exemplified mixture of at least two alkyl phenols having close boiling points is subjected to azeotropic distillation. It is essential to use an azeotroping agent selected from saturated aliphatic hydrocarbons of 9 to 13 carbon atoms having a boiling point of 150° to 190° C., preferably 160° to 180° C., at 760 mmHg. These saturated aliphatic hydrocarbons may be used singly or as a mixture of two or more.

The amount of the saturated aliphatic hydrocarbon can be selected as desired. For example, it is about 100 to about 5,000 parts by weight, preferably about 400 to about 2,000 parts by weight, per 100 parts by weight of the alkyl phenol mixture.

Specific examples of the hydrocarbon azeotroping agent include n-nonane (b.p. 151° C.), 2,6-dimethyloctane (b.p. 159° C.), n-decane (b.p. 174° C.), a mixture of decane isomers having a boiling point of from 150° to 190° C., a mixture of undecane isomers having a boiling range of 150° to 190° C., a mixture of dodecane isomers having a boiling range of 150° to 190° C., a mixture of tridecane isomers having a boiling range of 150° to 190° C., and 2,2,4,6,6-pentamethylheptane (b.p. 180° C.).

In the practice of this invention, another hydrocarbon solvent which is miscible with the above azeotroping agent and is not likely to form coloring substances under the azeotropic distillation conditions may be used together with the above-exemplified azeotroping agent. The amount of such a hydrocarbon solvent is less than the amount of the hydrocarbon azeotroping agent, preferably not more than 50% by weight of the azeotroping agent.

Examples of the azeotroping agent containing such a hydrocarbon solvent are hydrocarbon fractions boiling at 150° to 190° C. such as kerosene and light oils.

In the process of this invention, the above-exemplified mixture composed of at least two alkyl phenols having close boiling points can be separated into a higher-boiling alkyl phenol and a lower-boiling alkyl phenol with good efficiency by azeotropically distilling it in the presence of the above-described azeotroping agent. The distillation temperature may be any suitable temperature at which the lower-boiling alkyl phenol azeotropes, for example a temperature of about 150° to about 190° C. at atmospheric pressure.

The azeotropic distillation can be carried out under atmospheric, reduced or elevated pressures. Most commonly, the distillation is carried out at atmospheric pressure. Reduced pressures of up to about 50 mmHg, and elevated pressures of up to about 5000 mmHg can also be employed.

Distillation may be carried out continuously or batchwise. Separation of alkyl phenol from the resulting azeotrope (top) can be performed by a customary means such as steam distillation or crystallization.

The following Examples and Comparative Examples illustrate some modes of the practice of the present invention.

EXAMPLE 1 n-Decane ($C_{10}$) (113.6 g) was added to 86.4 g of crude 2,6-xylenol containing 13% by weight of o-cresol. The mixture was put into a 300 ml round-bottomed flask, and distilled at atmospheric pressure in an Oldershaw-type distillation column having 10 trays. Distillation began at 160° C. Ten milliliters of the initial fraction was isolated and analyzed by gas chromatography. The results are shown in Table 1.

No degeneration occurred in n-decane after heat-treatment at 180° C. for 6 hours under reflux.

EXAMPLE 2

Distillation was carried out under the same conditions as in Example 1 except that n-decane was replaced by dodecane isomers ($C_{12}$). The results are shown in Table 1.

The dodecane isomers were prepared as follows: To 200 g of reagent triisobutylene (a product of Tokyo Chemical Co., Ltd.) was added 20 g of 2%$Pd/Al_2O_3$, and the triisobutylene was hydrogenated at 150° C. under atmospheric pressure. The product had a boiling point of 177° C. at 760 mmHg.

No degeneration occurred in the dodecane isomers after heat-treatment at 180° C. for 6 hours under reflux.

EXAMPLE 3

Distillation was carried out under the same conditions as in Example 1 except that p-cresol was substituted for o-cresol. The results are shown in Table 1.

COMPARATIVE EXAMPLES 1, 2 AND 3

Distillation was carried out under the same conditions except that n-octane ($C_8$), n-undecane ($C_{11}$; b.p. about 196° C.) or triisobutylene ($C_{12}$ unsaturated) was used instead of the n-decane.

The triisobutylene was degenerated and colored (Mazen color: 140 APHA) after heat-treatment at 180° C. for 6 hours under reflux.

EXAMPLES 4 AND 5

Distillation was carried out under the same conditions except that 2,6-dimethyloctane ($C_{10}$) or 2,2,4,6,6-pentamethylheptane ($C_{12}$) was used instead of n-decane. The results are shown in Table 1.

The 2,6-dimethyloctane or 2,2,4,6,6-pentamethylheptane was not degenerated after heat-treatment at 180° C. for 6 hours under reflux.

TABLE 1

| | Azeotroping agent | | Composition of the starting mixture (wt. %) | | | Distillation temperature at the top (°C.) | Composition of the distillate (wt. %) | | | |
|---|---|---|---|---|---|---|---|---|---|---|
| | Type | Boiling point (°C. at 760 mmHg) | Additive | o-Cresol | 2,6-Xylenol | | Additive | o-Cresol | 2,6-Xylenol | APHA (*2) |
| Example 1 | n-Decane | 174 | 56.8 | 5.6 | 37.6 | 165 | 87.2 | 10.6 | 2.1 | 10 |
| Example 2 | Dodecane isomers | 177 | 56.5 | 5.6 | 37.9 | 171 | 81.3 | 15.2 | 3.5 | 10 |
| Example 3 | n-Decane | 174 | 56.5 | 5.6(*1) | 37.9 | 171 | 90.0 | 6.8(*1) | 3.2 | 10 |
| Comparative Example 1 | n-Octane | 126 | 56.5 | 5.6 | 37.9 | 126 | 99.6 | 0.3 | less than 0.1 | — |
| Comparative Example 2 | n-Undecane | 195.9 | 56.5 | 5.6 | 37.9 | 181 | 59.9 | 24.9 | 15.2 | — |
| Comparative Example 3 | Triisobutylene | 177 | 60.5 | 5.2 | 34.3 | 170 | 89.9 | 7.8 | 2.3 | 140 |
| Example 4 | 2,6-Dimethyloctane | 159 | 56.5 | 5.6 | 37.9 | 155 | 90.6 | 8.4 | 1.0 | 10 |
| Example 5 | 2,2,4,6,6-Pentamethyl- | 180 | 56.5 | 5.6 | 37.9 | 174 | 79.5 | 16.4 | 4.1 | 10 |

TABLE 1-continued

| Azeotroping agent | | Composition of the starting mixture (wt. %) | | | Distillation temperature at the top (°C.) | Composition of the distillate (wt. %) | | | |
|---|---|---|---|---|---|---|---|---|---|
| Type | Boiling point (°C. at 760 mmHg) | Additive | o-Cresol | 2,6-Xylenol | | Additive | o-Cresol | 2,6-Xylenol | APHA (*2) |
| heptane | | | | | | | | | |

(*1) p-Cresol
(*2) ASTM D-1209 (Hazen color)

What we claim is:

1. In a process for separating 2,6-xylenol and o-cresol by azeotropic distillation of a mixture of crude 2,6-xylenol containing o-cresol, the mixture being a methylated product of phenol or cresol, with a hydrocarbon azeotroping agent, the improvment comprising using as the hydrocarbon azeotroping agent one member of the group consisting of n-decane; dodecane isomers; 2,6-dimethyloctane; and 2,2,4,6,6-pentamethylheptane and removing the o-cresol as a top fraction, the 2,6-xylenol as a bottom fraction.

2. The process of claim 1 wherein the azeotropic distillation is carried out at atmospheric pressure.

* * * * *